(12) United States Patent
Sugawara et al.

(10) Patent No.: US 7,465,832 B2
(45) Date of Patent: Dec. 16, 2008

(54) METHOD OF PRODUCING XYLYLENEDIAMINE

(75) Inventors: Tomohiro Sugawara, Okayama (JP); Takafumi Abe, Kanagawa (JP); Tatsuyuki Kumano, Okayama (JP); Kinji Kato, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/749,787

(22) Filed: May 17, 2007

(65) Prior Publication Data

US 2007/0270613 A1    Nov. 22, 2007

(30) Foreign Application Priority Data

May 18, 2006    (JP)    ............................. 2006-138812

(51) Int. Cl.
*C07C 209/48*    (2006.01)
(52) U.S. Cl. .................................................... 564/385
(58) Field of Classification Search ........................ None
See application file for complete search history.

(56) References Cited

U.S. PATENT DOCUMENTS 3,647,054 A *  3/1972  Tsuboi et al. ................. 203/29
4,057,077 A    11/1977 Schabert et al.

FOREIGN PATENT DOCUMENTS

| EP | 1 449 825 A1 | 8/2004 |
|---|---|---|
| EP | 1 454 895 A1 | 9/2004 |
| JP | 51-024494 | 2/1976 |
| JP | 57-027098 | 2/1982 |
| JP | 2002-105035 | 4/2002 |
| JP | 2004-292435 | 10/2004 |
| WO | WO 2005/026098 A1 | 3/2005 |

OTHER PUBLICATIONS

European Search Report issued Jun. 2, 2008, for Application No. EP 07108328.1-1211.

\* cited by examiner

*Primary Examiner*—Brian J Davis
(74) *Attorney, Agent, or Firm*—Antonelli, Terry, Stout & Kraus, LLP.

(57) ABSTRACT

A method of producing xylylenediamine of the present invention includes the steps of: subjecting a liquid mixture of phthalonitriles with liquid ammonia or a mixture of liquid ammonia and an organic solvent to a first catalytic hydrogenation treatment, thereby hydrogenating the phthalonitriles to obtain a reaction product (A), wherein a content of the liquid ammonia or the mixture of liquid ammonia and an organic solvent is 80 wt % or more; removing the liquid ammonia in the reaction product (A) to obtain a reaction product (B); subjecting the reaction product (B) to a second catalytic hydrogenation treatment, thereby hydrogenating cyanobenzylamine to obtain a reaction product (C); and distilling the reaction product (C) to purify xylylenediamine.

5 Claims, No Drawings

METHOD OF PRODUCING XYLYLENEDIAMINE

This application claims priority under 35 U.S.C. §119 based upon Japanese Patent Application No. 2006-138812, filed in Japan on May 18, 2006.

BACKGROUND OF THE INVENTION

1. Field of the Invention

The present invention relates to a method of producing xylylenediamine which is useful as a resin curing agent and a raw material thereof, a polyamide resin, an isocyanate intermediate raw material, or the like.

2. Description of the Related Art

In recent years, high purity xylylenediamine having low cyanobenzylamine content is required as an isocyanate intermediate raw material, in particular. In such an application, high purity xylylenediamine having a cyanobenzylamine content of 0.02 wt % or less is required. Thus, a method of producing high purity xylylenediamine having low cyanobenzylamine content industrially and advantageously is required.

Xylylenediamine is known to be obtained through catalytic hydrogenation of phthalonitriles in the presence of liquid ammonia and/or an organic solvent (see JP 51-24494 A and JP 2002-105035 A). Phthalonitriles are compounds having relatively high melting points, and thus use of liquid ammonia or an organic solvent is required. In particular, liquid ammonia has conventionally been known to have an action of suppressing an undesirable side reaction in which an imine intermediate formed in a hydrogenation reaction and a nitrile group reacts to form an oligomer or the like. Thus, a large amount of liquid ammonia is often used.

Further, the catalytic hydrogenation reaction is a successive reaction in which phthalonitriles convert into cyanobenzylamine and then cyanobenzylamine converts into xylylenediamine. Thus, a trace amount of cyanobenzylamine always remains in a reaction system.

In the case where the catalytic hydrogenation reaction is conducted in a one-pass flow reaction or a batch reaction, a large amount of liquid ammonia must be used for suppressing a side reaction as described above. Thus, an apparent reaction rate is reduced due to reduction in a substrate concentration, and cyanobenzylamine is liable to remain in the reaction mixture. WO 2005/026098 describes a circular reaction system in which a part of reaction mixture from an outlet of reactor is mixed with a freshly fed raw material and returned to the inlet of the reactor for suppressing a use amount of a solvent. However, the substrate concentration is reduced even in this case, so cyanobenzylamine is liable to remain.

Cyanobenzylamine is an unstable substance which is liable to be colored and decomposed when left at stand, and forms a viscous substances through polymerization. Cyanobenzylamine in a state included in xylylenediamine also exhibits similar behaviors above mentioned and generally has a small difference in boiling points with that of corresponding xylylenediamine. Thus, separation of cyanobenzylamine through normal distillation involves difficulties.

Examples of a known method of producing xylylenediamine having low cyanobenzylamine content include: a method involving subjecting phthalonitriles to catalytic hydrogenation in the presence of liquid ammonia and/or an organic solvent, removing a solvent, and subjecting the thus-obtained crude xylylenediamine (a xylylenediamine having high cyanobenzylamine content) to alkali treatment (JP 45-14777 A, for example); and a method involving bringing crude xylylenediamine into contact with a catalyst containing an iron oxide or an oxide of iron and chromium in the presence of water (JP 57-27098 A, for example).

However, in the method involving alkali treatment, xylylenediamine having low cyanobenzylamine content can be obtained, but wastewater containing alkali is discharged. This wastewater is neutralized and then subjected to activated sludge treatment or incinerated treatment. However, there are many problems in such a treatment because of the alkali contained in the wastewater. The method involving bringing crude xylylenediamine into contact with a catalyst containing an iron oxide or an oxide of iron and chromium in the presence of water is industrially disadvantageous because the method requires a separate step of distilling off water used in a reaction or the like. Both methods are inefficient because cyanobenzylamine as an intermediate is converted into a high boiling point substance.

JP 2004-292435 A describes high purity xylylenediamine having low cyanobenzylamine content can be produced at high efficiency through hydrogenation of phthalonitriles in the presence of a solvent through two steps including: a step (a) of conducting a hydrogenation reaction until a conversion of nitrile groups reaches within a range of 90 mol % or more and less than 99.9 mol %; and a step (b) of conducting a hydrogenation reaction at a reaction temperature which is 10° C. or more higher than that of the step (a) to a higher nitrile conversion than that of the step (a) and 99.5 mol % or more.

This method is one method of obtaining high purity xylylenediamine having low cyanobenzylamine content. However, an undesirable side reaction takes place due to a high reaction temperature, and thus the nitrile conversion and reaction temperature in the step (a) must be adjusted for suppressing the side reaction, thereby involving complications in operation. Further, as a hydrogenation reaction is always conducted in the presence of a reaction solvent, and thus a considerable amount of a catalyst is required due to a low substrate concentration.

SUMMARY OF THE INVENTION

The present invention provides a method of producing high purity xylylenediamine having low cyanobenzylamine content, industrially and advantageously.

The inventors of the present invention have found that high purity xylylenediamine having low cyanobenzylamine content can be obtained at high efficiency by: subjecting phthalonitriles to a catalytic hydrogenation reaction (catalytic hydrogenation treatment) with liquid ammonia or a mixed solvent containing liquid ammonia and an organic solvent; removing at least liquid ammonia to obtain a reaction product once; subjecting the obtained reaction product to catalytic hydrogenation treatment again under mild conditions in the presence of a catalyst; and distilling and purifying the resultant.

That is, the present invention relates to a method of producing xylylenediamine including the steps of:

(1) subjecting a liquid mixture of phthalonitriles with liquid ammonia or a mixture of liquid ammonia and an organic solvent to a first catalytic hydrogenation treatment, thereby hydrogenating the phthalonitriles to obtain a reaction product (A), wherein a content of the liquid ammonia or the mixture of liquid ammonia and an organic solvent is 80 wt % or more;

(2) removing the liquid ammonia in the reaction product (A) to obtain a reaction product (B);

(3) subjecting the reaction product (B) to a second catalytic hydrogenation treatment, thereby hydrogenating cyanobenzylamine to obtain a reaction product (C); and (4) distilling the reaction product (C) to purify xylylenediamine.

DETAILED DESCRIPTION OF THE INVENTION

A production method of the present invention will be described by steps.

Step (1)

The step (1) refers to a step involving subjecting a liquid mixture of phthalonitriles with liquid ammonia or a mixture of liquid ammonia and an organic solvent to a first catalytic hydrogenation treatment, thereby hydrogenating the phthalonitriles to obtain a reaction product (A). A content of the liquid ammonia or the mixture of liquid ammonia and an organic solvent is 80 wt % or more.

The phthalonitriles used in the present invention each refer to a compound having two nitrile groups substituted in a benzene ring, or a compound having a halogen atom such as fluorine or chlorine, an alkyl group such as a methyl group or an ethyl group, or a phenyl group in addition to the two nitrile groups further substituted in a benzene ring.

Examples of the phthalonitriles include o-phthalonitrile, isophthalonitrile, terephthalonitrile, 2-chlorophthalonitrile, 5-methylisophthalonitrile, 4-methylisophthalonitrile, and 5-phenylisophthalonitrile, or the like.

Of those, isophthalonitrile, terephthalonitrile, and 4- and 5-methylisophthalonitrile are preferred, and isophthalonitrile and terephthalonitrile are more preferred.

In the present invention, the liquid mixture is subjected to the first catalytic hydrogenation treatment, and the phthalonitriles as described above are subjected to hydrogenation to obtain the reaction product (A). As a solvent, liquid ammonia or the mixture (hereinafter, sometimes referred to as "mixed solvent") containing liquid ammonia and an organic solvent is used.

As an organic solvent to be used in the mixed solvent, a low boiling point aromatic hydrocarbon or saturated aliphatic hydrocarbon capable of dissolving phthalonitriles is preferred. Specific examples thereof include benzene, toluene, xylenes, mesitylene, pseudocumene, hexane, and cyclohexane. Of those, xylenes are advantageous in industrial use.

A weight ratio of liquid ammonia to the organic solvent may arbitrarily be selected, but an amount of liquid ammonia is preferably equal to or more than that of phthalonitriles. A high ratio of the organic solvent can reduce a reaction pressure, but an excessively low ratio of liquid ammonia causes an undesirable side reaction and may reduce product yield.

As a catalyst for the catalytic hydrogenation reaction of phthalonitriles, a known supported metal catalyst or non-supported metal catalyst, a Raney catalyst, a precious metal catalyst, or the like may be used. In particular, a catalyst containing nickel, cobalt, or palladium is preferably used.

The first catalytic hydrogenation treatment may employ a batch system or a continuous system.

An example of the batch system is a complete mixing system in which a Raney metal powder catalyst of nickel or cobalt is introduced into a tank reactor.

An example of the continuous system is a system in which a tube reactor is used and a molded catalyst is used as a fixed bed. Further, a trickle-bed type continuous reactor into which the liquid mixture (raw material solution) and a hydrogen gas are supplied from the top of the reactor is used. This system is industrially simple and preferred. Note that the case where the trickle-bed type continuous reactor into which a raw material solution and a hydrogen gas are supplied from the top of the reactor is used may employ/a one-pass system in which the raw material solution and the hydrogen gas pass through the reactor for a reaction, or a circular system in which the raw material solution, a part of a reaction mixture from an outlet of the reactor, and the hydrogen gas pass through the reactor for a reaction.

During the first catalytic hydrogenation treatment, liquid ammonia or a mixed solvent containing liquid ammonia and an organic solvent is used in an amount of preferably 80 wt % or more and more preferably 90 wt % or more per the amount of the liquid mixture.

In the case where a use amount of liquid ammonia or a mixed solvent containing liquid ammonia and an organic solvent is less than 80 wt %, by-products are formed through an undesirable reaction and a product yield is reduced.

A ratio of liquid ammonia or a mixed solvent containing liquid ammonia and an organic solvent to the mixed solution is calculated from a charged composition of the raw material phthalonitriles and the solvent in the case of the batch reaction.

In the case of a flow reaction, the ratio is calculated from a composition of the raw material phthalonitriles and the solvent at an inlet of the reactor. That is, in the case of a circular system where the reaction product (A) is partly returned to the inlet of the reactor in the flow system, the ratio is calculated from a composition including the raw material solution to be freshly fed and the circulated reaction product (A).

A use amount of the catalyst varies depending on the kind of catalyst and reaction conditions, but in the batch system, the use amount thereof is preferably 0.1 to 200 parts by weight and more preferably 0.2 to 100 parts by weight per 100 parts by weight of initially charged amount of the raw material phthalonitriles. In the flow reaction system, the use amount of the catalyst is preferably 0.1 to 20,000 parts by weight and more preferably 0.2 to 7,000 parts by weight per 1 part by weight/hour of a supply speed of the raw material phthalonitriles.

A treatment temperature for the first catalytic hydrogenation treatment is preferably 20° C. to 200° C., more preferably 30° C. to 180° C., and furthermore preferably 40° C. to 150° C. Further, a hydrogen partial pressure is preferably 3.0 to 20.0 MPa, and more preferably 4.0 to 15.0 MPa.

Step (2)

The step (2) refers to a step involving removing the liquid ammonia in the reaction product (A) to obtain a reaction product (B).

Examples of a method of removing ammonia include a method involving pressure reduction, and a method involving passing an inert gas such as a nitrogen gas for removal.

In the case where the mixed solvent containing liquid ammonia and an organic solvent is used in the first catalytic hydrogenation treatment, liquid ammonia may be removed from the reaction product (A) by the method described above. The necessity of removing the organic solvent may arbitrarily be selected in consideration of an entire process. For removal of the organic solvent, distillation may be employed.

A total amount of xylylenediamine and cyanobenzylamine in the reaction product (B) is preferably 40 wt % or more, more preferably 60 wt % or more, and furthermore preferably 80 wt % or more. The total amount thereof of 40 wt % or more allows the following second catalytic hydrogenation treatment to be conducted under mild conditions.

In the step (2), the hydrogenation reaction doesn't take place because the hydrogen gas and the catalyst are absent. Therefore, the level of hydrogenation reaction of phthalonitriles in the step (1) can be estimated by analyzing the composition of reaction product (B). The amount of phthalonitriles in the reaction product (B) is preferably 100 ppm or less, and more preferably 10 ppm or less which is the analysis detection limit. When the amount of phthalonitriles is 100 ppm or less, the activity deterioration of the catalyst used for the second catalytic hydrogenation treatment can be suppressed. That is, it is meant that the level of hydrogenation reaction of phthalonitriles in the step (1) is a level of the hydrogenation to which 99.99 wt % or more of phthalonitriles convert.

A weight ratio of cyanobenzylamine to xylylenediamine in the reaction product (B) is preferably 0.01 or less. The weight ratio thereof of 0.01 or less may improve a quality of xylylenediamine to be obtained.

An amount of liquid ammonia in the reaction product (B) is preferably 1 wt % or less.

In the case where the amount of liquid ammonia is 1 wt % or less, increase of a partial pressure of the reaction product (B) can be prevented, and no high pressure reactor is required. Further, a smaller residual amount of liquid ammonia requires a small amount of a catalyst and allows efficient second catalytic hydrogenation treatment.

As described above, when the liquid ammonia used as a solvent is removed, a reaction pressure of the second catalytic hydrogenation treatment can be reduced. Further, a reaction rate is increased, and thus formation of cyanobenzylamine can be reduced with a small amount of the catalyst and a simple device.

Step (3)

The step (3) refers to a step involving subjecting the reaction product (B) to the second catalytic hydrogenation treatment, thereby hydrogenating cyanobenzylamine to obtain a reaction product (C).

In the second catalytic hydrogenation treatment, cyanobenzylamine in the reaction product (B) is hydrogenated into xylylenediamine. Thus, in this step, the cyanobenzylamine content can be further reduced.

Examples of a catalyst to be used for the second catalytic hydrogenation treatment include a supported metal catalyst, a non-supported metal catalyst, a Raney catalyst, and a precious metal catalyst. In particular, a catalyst containing nickel and/or cobalt supported on a support is preferred, and a nickel catalyst is more preferred. Examples of the support to be used include diatomaceous earth, silicon oxide, alumina, silica-alumina, titanium oxide, zirconium oxide, and carbon. In the case where the catalyst contains nickel and/or cobalt supported on a support, a nickel and/or cobalt content is preferably 10 to 80%, more preferably 30 to 70%, and furthermore preferably 40 to 60%.

The second catalytic hydrogenation treatment may employ a batch system or a continuous system. An example of the batch system is a complete mixing system in which a Raney metal powder catalyst of nickel or cobalt is introduced into a tank reactor for a reaction. An example of the continuous system is a system in which a tube reactor is used and a molded catalyst is used as a fixed bed. Further, a trickle-bed type continuous reactor in which a raw material (reaction product (B)) and a hydrogen gas are supplied from the top of the reactor is used. This system is industrially simple and preferred.

An example of material to be used in a catalytic hydrogenation reaction device for each of the first catalytic hydrogenation treatment and the second catalytic hydrogenation treatment is carbon steel or stainless steel such as SUS304, SUS316, or SUS316L. Further, a container obtained by subjecting iron or stainless steel to be used for a general pressure resistant container to glass lining treatment may be used.

A treatment temperature for the second catalytic hydrogenation treatment may appropriately be determined, but is preferably within a range of 30° C. to 150° C., and more preferably within a range of 40° C. to 100° C. The treatment temperature of 30° C. or higher can prevent significant reduction in cyanobenzylamine conversion. The treatment temperature of 150° C. or lower can prevent significant progress of nuclear hydrogenation and deamination of a large amount of xylylenediamine included in the reaction product (B) and can prevent heat modification of xylylenediamine itself.

In the second catalytic hydrogenation treatment, a hydrogen partial pressure is determined appropriately, but in general, the hydrogen partial pressure is preferably within a range of 0.1 to 10 MPa, more preferably within a range of 0.5 to 8 MPa, and furthermore preferably within a range of 1 to 4 MPa. The hydrogen partial pressure of 0.1 MPa or more can prevent significant reduction in cyanobenzylamine conversion. The hydrogen partial pressure of 10 MPa or less can prevent significant progress of nuclear hydrogenation and deamination of a large amount of xylylenediamine included in the reaction product (B).

In the case where the second catalytic hydrogenation treatment is conducted in a fixed-bed continuous flow system, a flow rate of the raw material to be introduced into a hydrogenation reactor is determined appropriately. A liquid space velocity (LHSV) is preferably within a range of 0.1 $h^{-1}$ to 10 $h^{-1}$, and more preferably within a range of 0.1 $h^{-1}$ to 3.0 $h^{-1}$. The liquid space velocity of 0.1 $h^{-1}$ or more can prevent an excessively low flow rate and prevent significant reduction in amount to be treated per hour, which is industrially advantageous. Further, progress of hydrocracking of a large amount of xylylenediamine included in the reaction product (B) can be prevented. The liquid space velocity of 10 $h^{-1}$ or less can prevent an excessively low cyanobenzylamine conversion and can maintain sufficient effects.

An amount of hydrogen in the second catalytic hydrogenation treatment may appropriately be determined. The amount varies depending on the cyanobenzylamine content in the reaction product (B), but is determined from a gas space velocity (GHSV) preferably within a range of 500 $h^{-1}$ or less and more preferably within a range of 200 $h^{-1}$ or less.

A weight ratio of cyanobenzylamine to xylylenediamine after the reaction product (B) is subjected to the second catalytic hydrogenation treatment is preferably 0.00005 or less. In the case where the weight ratio thereof is 0.00005 or less, a weight ratio of cyanobenzylamine to xylylenediamine after distillation and purification is easily adjusted to 0.00005 or less, and high quality xylylenediamine is obtained.

Step (4)

The step (4) refers to a step involving distilling the reaction product (C) to purify xylylenediamine.

A distillation device such as a packed tower, a plate column, or a flash drum can be employed for distilling, and distillation is conducted in a batch system or continuous system and preferably under reduced pressure. The reaction product (C) to be obtained after the second catalytic hydrogenation treatment contains both a compound having a lower boiling point than that of xylylenediamine and a compound having a higher boiling point than that of xylylenediamine. For removing both compounds, distillation and purification may be conducted by using two distillation columns including a low boiling point separation distillation column and a high boiling point separation distillation column. Alternatively, with use of one distillation column, a compound having a lower boiling point than that of xylylenediamine may be extracted from an overhead, and a compound having a higher boiling point than that of xylylenediamine can be extracted from a bottom. Further, xylylenediamine can be extracted from a middle part of the distillation column.

In the case where two distillation columns including a low boiling point separation distillation column and a high boiling point separation distillation column are used, a low boiling point compound may be removed in the low boiling point separation distillation column first, and then xylylenediamine can be obtained from an overhead of the high boiling point separation distillation column. Alternatively, a high boiling point compound may be removed in the high boiling point separation distillation column first, and then xylylenediamine can be obtained from a bottom of the low boiling point separation distillation column.

An operation pressure of the distillation column is preferably 1 to 30 kPa, and more preferably 1 to 10 kPa. A temperature at a bottom of the distillation device is preferably 80 to 195° C., and more preferably 100 to 185° C.

According to the production method of the present invention as described above, high quality xylylenediamine having very low cyanobenzylamine content can be obtained. Further, cyanobenzylamine can be removed under mild conditions. The amount of catalyst can be reduced, and a cost of constructing devices can be reduced. In the present invention, no water removal step is required.

EXAMPLES

Hereinafter, the present invention will be described in more detail with reference to examples, but the present invention is not limited to the examples in any way. Note that gas chromatography was used for composition analysis. A capillary electrophoresis device was used for analysis of a residual ammonia amount.

<Analysis Conditions for Gas Chromatography>
Device: 6890N, manufactured by Agilent Technologies, Inc.
GC column: DB-1, available from J&W Scientific
GC measurement sample: Each sample liquid was diluted with methanol, and diphenylmethane was added thereto as an internal standard for measurement.

<Analysis Conditions for Residual Ammonia Amount>
Device: Capillary Electrophoresis System, manufactured by Agilent Technologies, Inc.
Measurement sample: A sample was diluted 10 times with pure water for measurement (detection limit: about 10 ppm)

Example 1

Into a tubular vertical hydrogenation reactor having a volume of 400 ml, was packed 150 g of a commercially available supported nickel catalyst (Ni content of 50%), and this catalyst was subjected to hydrogen reduction. Then, a liquid mixture of isophthalonitrile and liquid ammonia (isophthalonitrile:liquid ammonia=8.5:91.5 (weight ratio)) was supplied from the top of the reactor at a rate of 170 g/h, and first catalytic hydrogenation treatment was conducted continuously at 70° C. for 10 days while 30 NL/h ("N" represents standard conditions, the same applies below) of a hydrogen gas was introduced at a reaction pressure of 7.0 MPa, to thereby produce a reaction product (A).

The reaction product (A) was passed through a gas-liquid separator, and a liquid phase part was extracted into a receiver intermittently. Ammonia was subjected to pressure reduction to a normal temperature and a normal pressure and removed from a gas phase part of the receiver. Then, a nitrogen gas was passed therethrough for an operation of removing residual ammonia, to thereby extract intermittently the reaction product (B). The extracted reaction product (B) was mixed completely, and then was analyzed by gas chromatography, and had metaxylylenediamine of 93.1 wt %, 3-cyanobenzylamine of 0.6 wt %, 3-methylbenzylamine of 0.02 wt %. No isophthalonitrile was detected. Remaining components were oligomers of metaxylylenediamine and polymers each having a high boiling point and not detected by gas chromatography. Note that the residual ammonia amount was about 500 ppm.

Into a tubular vertical hydrogenation reactor having a volume of 400 ml, was packed 150 g of a commercially available supported nickel catalyst (Ni content of 50%), and this catalyst was subjected to hydrogen reduction. Then, 1,800 g of the reaction product (B) obtained as described above was supplied from above top of the reactor at a rate of 75 g/h, and second catalytic hydrogenation treatment was conducted at 80° C. while 3 NL/h of a hydrogen gas was introduced at a reaction pressure of 2.0 MPa. A gas and a liquid were separated, and then the reaction product (C) was extracted. The reaction product (C) was analyzed by gas chromatography, and had a metaxylylenediamine concentration of 93.5 wt %, a 3-methylbenzylamine concentration of 0.04 wt %, and a 3-cyanobenzylamine concentration of 0.001 wt % or less.

The obtained reaction product (C) was subjected to distillation under reduced pressure of 6 kPa by using a distillation column with a theoretical plate number of 10, to thereby obtain metaxylylenediamine purified to have a purity of 99.99%. Note that a 3-cyanobenzylamine content in the obtained metaxylylenediamine was 0.001 wt % or less.

Example 2

Into a tubular vertical hydrogenation reactor having a volume of 400 ml, was packed 150 g of a commercially available supported nickel catalyst (Ni content of 50%), and this catalyst was subjected to hydrogen reduction. Then, 1,500 g of the reaction product (B) obtained in Example 1 was supplied from the top of the reactor at a rate of 150 g/h, and the second catalytic hydrogenation treatment was conducted at 100° C. while 3 NL/h of a hydrogen gas was introduced at a reaction pressure of 2.0 MPa. A gas and a liquid were separated, and then the reaction product (C) was extracted. The reaction product (C) was analyzed by gas chromatography, and had a metaxylylenediamine concentration of 93.4 wt %, a 3-methylbenzylamine concentration of 0.06 wt %, and a 3-cyanobenzylamine concentration of 0.001 wt % or less. Remaining components were oligomers of metaxylylenediamine and polymers each having a high boiling point and not detected by gas chromatography.

The obtained reaction product (C) was subjected to distillation in the same manner as in Example 1, to thereby obtain metaxylylenediamine purified to have a purity of 99.99%. Note that the 3-cyanobenzylamine content in the obtained metaxylylenediamine was 0.001 wt % or less.

Example 3

Into a tubular vertical hydrogenation reactor having a volume of 400 ml, was packed 150 g of a commercially available supported nickel catalyst (Ni content of 50%), and this catalyst was subjected to hydrogen reduction. Then, a liquid mixture of isophthalonitrile, metaxylene, and liquid ammonia (isophthalonitrile:metaxylene:liquid ammonia=6:10:84 (weight ratio)) was supplied from the top of the reactor at a rate of 240 g/h, and the first catalytic hydrogenation treatment was conducted continuously at 70° C. for 7 days while 30

NL/h of a hydrogen gas was introduced at a reaction pressure of 7.0 MPa, to thereby produce a reaction product (A).

The reaction product (A) was passed through a gas-liquid separator, and a liquid phase part was extracted into a receiver intermittently. Ammonia was subjected to pressure reduction to a normal temperature and a normal pressure and removed from a gas phase part of the receiver. Then, a nitrogen gas was passed therethrough for an operation of removing residual ammonia, to thereby extract intermittently the reaction product (B). The extracted reaction product (B) was mixed completely, and then metaxylylene was distilled off with a rotary evaporator. The reaction product (B) after distillation was analyzed by gas chromatography, and had metaxylylenediamine of 92.8 wt %, 3-cyanobenzylamine of 0.8 wt %, 3-methylbenzylamine of 0.01 wt %, and metaxylylene of 0.9 wt %. No isophthalonitrile was detected. Remaining components were oligomers of metaxylylenediamine and polymers each having a high boiling point and not detected by gas chromatography. Note that the residual ammonia amount was below the detection limit.

Into a tubular vertical hydrogenation reactor having a volume of 400 ml, was packed 150 g of a commercially available supported nickel catalyst (Ni content of 50%), and this catalyst was subjected to hydrogen reduction. Then, 1,500 g of the reaction product (B) obtained as described above was supplied from the top of the reactor at a rate of 150 g/h, and second catalytic hydrogenation treatment was conducted at 100° C. while 3 NL/h of a hydrogen gas was introduced at a reaction pressure of 4.0 MPa. A gas and a liquid were separated, and then the reaction product (C) was extracted. The reaction product (C) was analyzed by gas chromatography, and had a metaxylylenediamine concentration of 92.9 wt %, a 3-methylbenzylamine concentration of 0.09 wt %, and a 3-cyanobenzylamine concentration of 0.001 wt % or less.

The obtained reaction product (C) was subjected to distillation in the same manner as in Example 1, to thereby obtain metaxylylenediamine purified to have a purity of 99.99%. Note that the 3-cyanobenzylamine content in the obtained metaxylylenediamine was 0.001 wt % or less.

Example 4

Into a tubular vertical hydrogenation reactor having a volume of 400 ml, was packed 150 g of a commercially available supported nickel catalyst (Ni content of 50%), and this catalyst was subjected to hydrogen reduction. Then, a liquid mixture of isophthalonitrile and liquid ammonia (isophthalonitrile:liquid ammonia=1:3 (weight ratio)) was supplied to the reactor at a rate of 57.8 g/h. Meanwhile, a part of a reaction liquid was extracted from a liquid pool provided on a lower part of the reactor, subjected to pressure increase with a gear pump, and circulated at 173.4 g/hr through a liquid mass flow meter, and supplied from the top of the reactor together with the newly charged raw material (unused liquid mixture) describe above. The first catalytic hydrogenation treatment was conducted continuously at 70° C. for 10 days while 30 NL/h of a hydrogen gas was introduced at a reaction pressure of 7.0 MPa, to thereby produce a reaction product (A).

An amount of liquid ammonia at an inlet of the reactor (57.8 g/h×3/4+173.4 g/h×3/4=173.4 g/h) was 92 wt % per the amount of the liquid mixture of liquid ammonia and isophthalonitrile (173.4 g/h+57.8 g/h×1/4=187.8 g/h).

The reaction product (A) was passed through a gas-liquid separator, and a liquid phase part was extracted into a receiver intermittently. Ammonia was subjected to pressure reduction to a normal temperature and a normal pressure and was removed from a gas phase part of the receiver. Then, a nitrogen gas was passed therethrough for an operation to remove residual ammonia, to thereby extract intermittently the reaction product (B).

The extracted reaction product (B) was mixed completely, and then was analyzed by gas chromatography. The reaction product (B) had metaxylylenediamine of 92.8 wt %, 3-cyanobenzylamine of 0.7 wt %, and 3-methylbenzylamine of 0.02 wt %. No isophthalonitrile was detected. Remaining components were oligomers of metaxylylenediamine and polymers each having a high boiling point and not detected by gas chromatography. Note that the residual ammonia amount was about 500 ppm.

The reaction product (B) was subjected to the second catalytic hydrogenation treatment under the same conditions as those of Example 1. A gas and a liquid were separated, and then the reaction product (C) was extracted. The reaction product (C) was analyzed by gas chromatography, and had a metaxylylenediamine concentration of 93.2 wt %, a 3-methylbenzylamine concentration of 0.04 wt %, and a 3-cyanobenzylamine concentration of 0.001 wt % or less.

The obtained reaction product (C) was subjected to distillation in the same manner as in Example 1, to thereby obtain metaxylylenediamine purified to have a purity of 99.99%. Note that the 3-cyanobenzylamine content in the obtained metaxylylenediamine was 0.001 wt % or less.

Example 5

An autoclave equipped with a jacket and having a volume of 5 L was subjected to nitrogen replacement. Then, 30 g of a commercially available supported nickel catalyst (Ni content of 50%) reduced in a stream of hydrogen at 200° C. in advance and 1,500 g of a solution of liquid ammonia containing 8.5 wt % of isophthalonitrile was charged into the autoclave, and the autoclave was subjected to pressure increase to 6.0 MPa at room temperature with a hydrogen gas. Then, hot water was passed through the jacket under stirring, and a liquid temperature was increased to 80° C. An inner pressure of the autoclave was increased once with heating. Then, absorption of hydrogen began, and the pressure was reduced. Thus, a hydrogen gas was intermittently supplied. The liquid temperature was maintained at 80° C., and the inner pressure was maintained at 7.0 to 8.0 MPa for the first catalytic hydrogenation treatment.

After observation of no pressure reduction in the autoclave, the reaction was continued at a liquid temperature of 80° C. for an additional hour. Then, water was passed through the jacket to reduce the liquid temperature to room temperature, and the hydrogen gas and a part of ammonia were removed from a gas phase part of the autoclave to a normal pressure while water was passed through the jacket, to thereby obtain a reaction product (A). After leaving at stand for 2 hours, the reaction product (A) was transferred to another autoclave having a volume of 5 L through an in-line filter. After the transfer, ammonia was removed at normal pressure until no pressure increase was observed while a nitrogen gas was passed through the liquid.

Then, the liquid in the autoclave was extracted, and 130 g of the reaction product (B) was obtained. The reaction product (B) was analyzed by gas chromatography, and had metaxylylenediamine of 91.2 wt %, 3-cyanobenzylamine of 0.5 wt %, and 3-methylbenzylamine of 0.05 wt %. No isophthalonitrile was detected. Remaining components were oligomers of metaxylylenediamine and polymers each having a high boiling point and not detected by gas chromatography. Note that the residual ammonia amount was about 300 ppm.

Into a tubular vertical hydrogenation reactor having a volume of 30 ml, was packed 15 g of a commercially available supported nickel catalyst (Ni content of 50%), and this catalyst was subjected to hydrogen reduction. Then, 100 g of the reaction product (B) obtained as described above was supplied from the top of the reactor at a rate of 7.5 g/h, and second catalytic hydrogenation treatment was conducted at 80° C. while 3 NL/h of a hydrogen gas was introduced at a reaction pressure of 2.0 MPa. A gas and a liquid were separated, and then a liquid was extracted, to thereby obtain 80 g of the reaction product (C). The reaction product (C) was analyzed by gas chromatography, and had a metaxylylenediamine concentration of 91.3 wt %, a 3-methylbenzylamine concentration of 0.07 wt %, and a 3-cyanobenzylamine concentration of 0.001 wt % or less.

The obtained reaction product (C) was subjected to distillation in the same manner as in Example 1, to thereby obtain metaxylylenediamine purified to have a purity of 99.99%. Note that the 3-cyanobenzylamine content in the obtained metaxylylenediamine was 0.001 wt % or less.

Comparative Example 1

Into a tubular vertical hydrogenation reactor having a volume of 400 ml, was packed 150 g of a commercially available supported nickel catalyst (Ni content of 50%), and this catalyst was subjected to hydrogen reduction. Then, a liquid mixture of isophthalonitrile and liquid ammonia (isophthalonitrile:liquid ammonia=1:3 (weight ratio)) was supplied from the top of the reactor at a rate of 57.8 g/h, and the first catalytic hydrogenation treatment was conducted continuously at 70° C. for 10 days while 30 NL/h of a hydrogen gas was introduced at a reaction pressure of 7.0 MPa, to thereby produce a reaction product (a).

The reaction product (a) was passed through a gas-liquid separator, and a liquid phase part was extracted into a receiver intermittently. Ammonia was subjected to pressure reduction to a normal temperature and a normal pressure and was removed from a gas phase part of the receiver. Then, a nitrogen gas was passed therethrough for an operation of removing residual ammonia, to thereby extract intermittently the reaction product (b).

The extracted reaction product (b) was mixed completely, and then was analyzed by gas chromatography. The reaction product (b) had metaxylylenediamine of 85.3 wt %, 3-cyanobenzylamine of 0.03 wt %, and 3-methylbenzylamine of 0.7 wt %. No isophthalonitrile was detected. Remaining components were oligomers of metaxylylenediamine and polymers each having a high boiling point and not detected by gas chromatography. Note that the residual ammonia amount was about 500 ppm.

In this way, in the case where the amount of the solvent containing liquid ammonia was excessively small in the first catalytic hydrogenation treatment, the amount of cyanobenzylamine was small. However, large amounts of polymers were produced through a side reaction, and the yield of xylylenediamine was reduced significantly.

What is claimed is:

1. A method of producing xylylenediamine, comprising the steps of:
   (1) subjecting a liquid mixture of phthalonitriles with liquid ammonia or a mixture of liquid ammonia and an organic solvent to a first catalytic hydrogenation treatment, thereby hydrogenating the phthalonitriles to obtain a reaction product (A), wherein a content of the liquid ammonia or the mixture of liquid ammonia and an organic solvent is 80 wt % or more;
   (2) removing the liquid ammonia in the reaction product (A) to obtain a reaction product (B);
   (3) subjecting the reaction product (B) to a second catalytic hydrogenation treatment, thereby hydrogenating cyanobenzylamine to obtain a reaction product (C); and
   (4) distilling the reaction product (C) to purify xylylenediamine.

2. A method of producing xylylenediamine according to claim 1, wherein the reaction product (C) has a weight ratio of cyanobenzylamine to xylylenediamine of 0.00005 or less.

3. A method of producing xylylenediamine according to claim 1, wherein the reaction product (B) has a weight ratio of cyanobenzylamine to xylylenediamine of 0.01 or less.

4. A method of producing xylylenediamine according to claim 1, wherein the content of one of liquid ammonia, and liquid ammonia and an organic solvent in the liquid mixture is 90 wt % or more.

5. A method of producing xylylenediamine according to claim 1, wherein the second catalytic hydrogenation treatment is conducted in the presence of a nickel catalyst and/or a cobalt catalyst.

* * * * *